United States Patent [19]

Telschow

[11] Patent Number: 5,486,640

[45] Date of Patent: Jan. 23, 1996

[54] PROCESS FOR PREPARING BIS(PENTAERYTHRITOL PHOSPHATE ALCOHOL) ALKYLPHOSPHONATE

[75] Inventor: Jeffrey E. Telschow, Tarrytown, N.Y.

[73] Assignee: Akzo Nobel NV, Arnhem, Netherlands

[21] Appl. No.: 298,249

[22] Filed: Aug. 30, 1994

Related U.S. Application Data

[62] Division of Ser. No. 155,666, Nov. 22, 1993, Pat. No. 5,362,898.

[51] Int. Cl.$^6$ .................................................... C07F 9/02
[52] U.S. Cl. .................................................... 558/74; 558/98
[58] Field of Search .................................... 558/98, 74

[56] References Cited

U.S. PATENT DOCUMENTS

| | | | |
|---|---|---|---|
| 3,494,986 | 2/1970 | Hechenbleikner | 558/98 |
| 3,772,414 | 11/1973 | Baker et al. | 558/98 |
| 3,789,091 | 1/1974 | Anderson et al. | 260/927 R |
| 3,883,478 | 5/1975 | Gresham | 260/45.8 R |
| 3,965,220 | 6/1976 | Schumacher | 558/98 |
| 4,152,373 | 5/1979 | Honig et al. | 260/969 |
| 4,801,625 | 1/1989 | Parr et al. | 523/179 |
| 5,235,085 | 8/1993 | Telschow et al. | 558/74 |
| 5,237,085 | 8/1993 | Telschow et al. | 558/74 |

FOREIGN PATENT DOCUMENTS

866204   3/1971   Canada .................................. 260/346

OTHER PUBLICATIONS

J. Org. Chem. vol. 42, No. 2 (1977) pp. 379–381.

*Primary Examiner*—James H. Reamer
*Attorney, Agent, or Firm*—Richard P. Fennelly; Louis A. Morris

[57] ABSTRACT

A bis(pentaerythritol phosphate alcohol) alkylphosphonate compound, such as one comprising an alkyl group of from about one to four carbon atoms, preferably bis(pentaerythritol phosphate alcohol) methylphosphonate, is a flame retardant compound. Such a compound can be prepared by the transesterification of a diphenyl alkyl phosphonate carrying the desired alkyl group with pentaerythritol phosphate alcohol. An alternative process of preparation comprises the reaction of pentaerythritol phosphate alcohol, a trialkylamine, and an alkylphosphonic dihalide.

3 Claims, No Drawings

PROCESS FOR PREPARING BIS(PENTAERYTHRITOL PHOSPHATE ALCOHOL) ALKYLPHOSPHONATE

This is a continuation division of application Ser. No. 08/155,666 filed Nov. 22, 1993 now U.S. Pat. No. 5,362,898.

BACKGROUND OF THE INVENTION

Various derivatives of pentaerythritol phosphate are known as flame retardant additives for polymers such as polypropylene. A recent example is provided by U.S. Pat. No. 4,801,625 to W. J. Parr et al. which describes ether, ester and carbonate derivatives of pentaerythritol phosphate. The carbonate version of such compounds can be advantageously prepared by the reaction of pentaerythritol phosphate alcohol with a dihydrocarbyl carbonate as described in U.S. Pat. No. 5,235,085.

SUMMARY OF THE PRESENT INVENTION

The present invention relates to novel flame retardant compounds which are bis(pentaerythritol phosphate alcohol) alkylphosphonate compounds.

DESCRIPTION OF PREFERRED EMBODIMENTS

The present novel bis(pentaerythritol phosphate alcohol) alkylphosphonate compounds are of the formula:

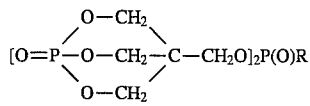

where R is alkyl, for example alkyl of from one to four carbon atoms, preferably methyl.

One process for forming the above-described novel compounds is by the transesterification of a diphenyl alkyl phosphonate carrying the desired alkyl group with pentaerythritol phosphate alcohol which has the formula

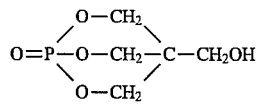

The phosphonate reagent is of the formula $(ArO)_2P(O)R$, where Ar is substituted or unsubstituted phenyl and R is alkyl as previously described. The transesterification reaction is advantageously conducted at elevated temperature (e.g., a temperature of from about 170° C. to about 200° C.) in a high boiling organic solvent, such as an aryl phosphate solvent, (as described in U.S. Pat. No. 5,237,085), using an appropriate transesterification catalyst (e.g., magnesium dichloride, sodium phenoxide, or the like). The reaction mixture will contain the desired crude product with a phenolic by-product. The crude product can be triturated with a solvent such as acetonitrile or methanol to give the desired, purified product.

An alternative way of preparing the novel compounds is by the reaction of pentaerythritol phosphate alcohol, a trialkylamine, such as triethylamine, and an alkylphosphonic dihalide, such as methylphosphonic dichloride, in an appropriate solvent, such as acetonitrile, under cooling at essentially ambient temperature (e.g., 20° C. to about 30° C.).

The following Examples further illustrate the present invention.

EXAMPLE 1

This illustrates preparation of bis(pentaerythritol phosphate alcohol) methylphosphonate.

Pentaerythritol phosphate alcohol (90.1 gm, 0.5 mole), diphenyl methylphosphonate (62.0 gm, 0.25 mole), magnesium chloride (238 mg, 2.5 mmole, 1.0 mole % on diphenyl methylphosphonate), and 85 mL of isopropyl triarylphosphate (PHOSFLEX 41P brand from Akzo Chemicals Inc.) were charged to a 250 mL, four neck, round bottom flask with mechanical stirrer, thermometer, 3.5 inch Vigreux column, distillation head and receiver with vacuum connection. A vacuum of 60 mm Hg was applied, and the reaction mixture was heated.

Over a period of four hours the flask temperature was raised from room temperature to 193° C. About thirty-five minutes thereafter, slow distillation of phenol began at a flask temperature of 185° C., distillation head temperature of 97°C., and 35 mm Hg pressure. One hour later, with the flask at 200°C., the distillation head at 90° C., and 10 mm Hg pressure, the reaction was cooled and 1000 mg of magnesium chloride was added. Then, the reactor was heated for two hours at 195° C. (down to 5.5 mm Hg pressure) before cooling after no further distillation occurred.

The system was cooled to 100° C. at which time two phases were observed, one liquid and the other a gummy mass. After further cooling to 80° C., 100 ml of methanol was added which dissolved the liquid phase and part of the gummy mass leaving behind a white solid. The solid was removed by filtration and washed three times with 20 ml of methanol. The washed product was dried in an oven overnight at room temperature and 1 mm Hg pressure yielding 12.0 gm of a white powder having a decomposition about 325° C.

After the remaining mother liquor was allowed to stand overnight, more solid crystallized and was filtered, washed twice with 20 ml of methanol, and dried in air to yield 5.8 gm of a white solid.

Both isolated products had structures by $^{31}p$ nmr in DMSO (+34.2 ppm and −6.3 ppm in a 1:2 ratio) which were consistent with bis(pentaerythritol phosphate alcohol) methylphosphonate.

EXAMPLE 2

This illustrates an alternative preparation of bis(pentaerythritol phosphate alcohol) methylphosphonate.

Pentaerythritol phosphate alcohol (63.4 g, 0.36 mole), triethylamine (49.1 mL, 35.6 g, 0.36 mole), and 150 mL of acetonitrile were charged to a 250 mL 4-necked round-bottomed flask with mechanical stirrer, thermometer, nitrogen inlet, and dropping funnel containing methylphosphonic dichloride (23.4 g, 0.18 mole) and 5 mL acetonitrile. The reactor was stirred and cooled with an ice bath as the methylphosphonic dichloride was added dropwise over fifteen minutes while maintaining a pot temperature of 20° C.–30° C.

The resulting thick slurry was heated to reflux for twelve hours, cooled to 25° C., and filtered. The white solid was washed four times with 50 mL of methanol and then dried overnight at 100° C./2 mm Hg. The white product weighed 61.4 g (81.2 % yield) and had properties substantially identical to the product from Example 1.

EXAMPLES 3–5

The compound of Example 2, hereinafter abbreviated as "Bis(PEPA)MP" was evaluated as a flame retardant in polypropylene in the three formulations listed below from the following ingredients.

| Ingredient | Weight Percentage | | |
|---|---|---|---|
| | 1 | 2 | 3 |
| Polypropylene* | 71.1 | 71.1 | 68.7 |
| Bis(PEPA)MP | 10.9 | 10.9 | 12.0 |
| APP** | 18.0 | — | — |
| MPP*** | — | 18.0 | 19.8 |

*Polypropylene homopolymer powder from Himont (PROFAX 6623PM brand)
**Ammonium polyphosphate from Monsanto (P/40 brand).
***Melamine phosphate from Akzo Chemicals Inc. (FYROL MP brand).

All ingredients were preblended prior to compounding in a Brabender mixer bowl. The mixing regime was at a temperature of 164° C. for approximately five minutes at a rotor rate of 50–75 rpm. The homogenized mixture was then compression molded to a thickness of 1/16" in a heated hydraulic press (200° C.) for three-five minutes and cooled to room temperature. From this molded plaque, UL-94 test specimens were cut and tested for flammability.

The flame retardancy data was as follows:

| Result | 1 | 2 | 3 |
|---|---|---|---|
| UL-94 Test | V-2 | V-2 | V-0 |
| Average Flame Time (sec) | 2.1 | 8.9 | 1.2 |

I claim:

1. A process for preparing a bis(pentaerythritol phosphate alcohol) alkylphosphonate compound which comprises the reaction of pentaerythritol phosphate alcohol, a trialkylamine, and an alkylphosphonic dihalide.

2. A process as claimed in claim 1 wherein the alkyl group in the alkylphosphonic dihalide contains from about one to four carbon atoms.

3. A process as claimed in claim 1 wherein the compound which is prepared is bis(pentaerythritol phosphate alcohol) methylphosphonate.

* * * * *